United States Patent [19]

Evani et al.

[11] Patent Number: 4,535,098

[45] Date of Patent: Aug. 13, 1985

[54] MATERIAL FOR ABSORBING AQUEOUS FLUIDS

[75] Inventors: Syamalarao Evani, Midland; James H. Oswald, Auburn; Thomas L. Staples; Brent T. Polak, both of Midland, all of Mich.

[73] Assignee: The Dow Chemical Company, Midland, Mich.

[21] Appl. No.: 588,483

[22] Filed: Mar. 12, 1984

[51] Int. Cl.$^3$ ............................................. C08L 31/02
[52] U.S. Cl. ..................................... 521/149; 524/560; 524/561; 526/317; 604/368; 604/378
[58] Field of Search ................ 521/149; 524/560, 561; 526/317; 604/368, 378

[56] References Cited

U.S. PATENT DOCUMENTS

| | | | |
|---|---|---|---|
| 3,926,891 | 12/1975 | Gross et al. | 526/271 |
| 4,062,817 | 12/1977 | Westerman | 526/271 |
| 4,066,583 | 1/1978 | Spaulding | 526/47 |
| 4,190,562 | 2/1980 | Westerman | 526/319 |
| 4,293,609 | 10/1981 | Erickson | 428/286 |
| 4,304,902 | 12/1981 | Landoll | 528/419 |
| 4,432,881 | 2/1984 | Evani | 524/401 |

*Primary Examiner*—Maurice J. Welsh

[57] ABSTRACT

Water absorbent compositions comprise a water swellable polymer which contains polymerized water-soluble monomers, water-insoluble monomers having a pendant hydrophobic moiety, and optionally, a cross-linking monomer. The polymer can be blended with a colloidal support such as colloidal silica. The compositions exhibit good water absorbency rates and high gel strengths.

27 Claims, No Drawings

MATERIAL FOR ABSORBING AQUEOUS FLUIDS

BACKGROUND OF THE INVENTION

The present invention relates to water-swellable polymers which polymers are useful in absorbing aqueous fluids.

Water absorbent materials comprising water-swellable polymers have provided various uses in the art. See, for example, U.S. Pat. Nos. 3,926,891; 4,190,562; 4,293,609 and 4,424,247. Numerous disposable articles containing such water-swellable polymers are disclosed as in U.S. Pat. Nos. 3,669,103 and 3,888,257.

Water-swellable polymers which are useful in providing absorbent materials are typically polymers comprising crosslinked acrylamide; hydrolyzed acrylamide; acrylic acid; hydrolyzed acrylates; hydrolyzed acrylonitrile; and grafted starch and celluloses; and the like. Such polymers require considerable care in controlling the amount of crosslinking which is present. For example, if the amount of crosslinking in the polymer is increased, the gel strength of the resulting polymer network is increased at the expense of reducing the capacity of the gel to absorb fluid. On the other hand, at low degrees of crosslinking the gels have a poor, slimy consistency which exhibit low gel strengths.

In view of the fact that the utility of known water-absorbent materials is limited due to lack of integrity of the gel structure during use, insufficient absorbing capacity and absorbing rate, and difficulties in crosslinking the polymers which are employed; it would be highly desirable to provide a novel, highly absorbent polymer system having a high gel strength and minimal amounts of crosslinking.

SUMMARY OF THE INVENTION

The present invention is a composition capable of absorbing an aqueous liquid which composition comprises a functionally effective amount of a swellable addition polymer comprising, in polymerized form, (a) a major portion of at least one water-soluble monomer, (b) a minor portion of at least one water-insoluble monomer having a pendant hydrophobic moiety and, optionally, (c) a minor portion of crosslinkable monomer in an amount sufficient to provide gel strength to the polymer; which polymer is polymerized in the presence of at least a micelle forming amount of a surfactant composition containing at least one ionic surfactant; and which polymer is capable of undergoing hydrophobic association through hydrophobic groups of said polymer such that said polymer is swellable but not readily soluble in the presence of an aqueous liquid when said polymer is in intimate contact with an amount of surfactant, if any, which is less than that amount of surfactant which will solubilize said polymer in said aqueous liquid.

In another aspect, the present invention is a composition capable of absorbing an aqueous liquid which composition comprises a functionally effective amount of an inorganic colloidal support which is contacted with the polymer of this invention.

The compositions of this invention, which have absorbed aqueous fluids, exhibit gel strengths which can increase with time. That is, swollen gel particles of this invention in contact with one another are capable of forming one large continuous gel particle by what is believed to be intergel associations. This expected change in structure of the gel provides an increase in gel strength of the gel as a whole. In addition, the formation of a large gel particle provides a gel having less tendency to migrate during use. Gels of this invention have improved adhesive and elasticity characteristics.

The compositions of this invention are capable of absorbing many times their own weight of an aqueous fluid. That is, the compositions of this invention can have improved aqueous fluid absorbing capacity, exhibit improved rates of aqueous fluid absorption, and have improved gel strengths. Consequently, the compositions are useful in providing a process for absorbing large amounts of an aqueous fluid. The compositions are useful in a wide variety of applications wherein water-absorbent polymeric materials have been used.

DETAILED DESCRIPTION OF THE ILLUSTRATIVE EMBODIMENTS

By "hydrophobic associative" is meant that, in aqueous media, the pendant hydrophobic moieties of the polymer associate thereby preventing solubilization and providing swellability of the polymer in an aqueous medium.

The hydrophilic/hydrophobic polymer (i.e., water swellable addition polymer) is predominantly hydrophilic, but contains a sufficient concentration of suitable hydrophobic moieties to enable it to associate with other hydrophobic moieties and the hydrophobic moieties of any surfactant which is present to cause a substantial swellability of the polymer in the presence of an aqueous medium. That is, the hydrophilic monomers polymerize to form a major portion of the polymer and the hydrophobic monomers polymerize to form a minor portion of the polymer. The polymer has an unassociated molecular weight which can vary such that the polymer will form a gel. Polymers having very high molecular weight, e.g., weight average molecular weight greater than 5 million, are believed to be suitably employed. Preferably, the hydrophilic/hydrophobic polymers used in this invention have weight average molecular weights in the range from about 200,000 to about 10 million, most preferably from about 800,000 to about 5 million. See U.S. Pat. No. 4,432,881, which is incorporated herein by reference.

The hydrophobic groups of the hydrophilic/hydrophobic polymer are preferably pendant organic groups having hydrophobicities comparable to one of the following: aliphatic hydrocarbon groups having at least about four carbons such as $C_4$ to $C_{20}$ alkyls and cycloalkyls; aromatic and aromatic hydrocarbon groups such as naphthyls; alkylaryls wherein alkyl has one or more carbons, preferably 4 to 8 carbons; haloalkyls of 4 or more carbons, preferably perfluoroalkyls; polyalkyleneoxy groups wherein alkylene is propylene or higher alkylene and there is at least 1 alkyleneoxy unit per hydrophobic moiety.

Suitable hydrophobic monomers include those which are (1) water-insoluble, i.e., less than about 0.4, preferably about 0.2 weight part of the hydrophobic monomer will dissolve in 100 weight parts water and (2) ethylenically unsaturated compounds having hydrophobic groups as defined hereinbefore. Exemplary hydrophobic monomers include the higher alkyl esters of $\alpha,\beta$-ethylenically unsaturated carboxylic acids such as dodecyl acrylate, dodecyl methacrylate, tridecyl acrylate, tridecyl methacrylate, tetradecyl acrylate, tetradecyl methacrylate, octadecyl acrylate, octadecyl methacylate, ethyl half ester of maleic anhydride, diethyl maleate, and other alkyl esters derived from the reactions of alkanols having from 4 to about 20, preferably from 8 to about 20, carbon atoms with ethylenically unsaturated carboxylic acids such as acrylic acid, methacrylic acid, fumaric acid, itaconic acid and aconitic acid, and maleic anhydride; alkylaryl esters of ethylenically unsaturated carboxylic acids such as nonyl-α-phenyl acrylate, nonyl-α-phenyl methacrylate, dodecyl-α-phenyl acrylate and dodecyl-α-phenyl methacrylate; N-alkyl, ethylenically unsaturated amides such as N-octadecyl acrylamide, N-octadecyl methacrylamide, N,N-dioctyl acrylamide and similar derivatives thereof; α-olefins such as octene-1-, decene-1, dodecene-1 and hexadecene-1; vinyl alkylates wherein alkyl has at least 8 carbons such as vinyl laurate and vinyl stearate; vinyl alkyl ethers such as dodecyl vinyl ether and hexadecyl vinyl ether; N-vinyl amides such as N-vinyl lauramide and N-vinyl stearamide; and ar-alkylstyrenes such as t-butyl styrene. Of the foregoing hydrophobic monomers, the alkyl esters of acrylic acid, methacrylic acid, N-alkyl acrylamides and N-alkyl methacrylamides wherein alkyl has from 8 to 20 carbon atoms, styrene and the alkyl styrenes wherein alkyl has from 4 to 8 carbons such as t-butyl, are preferred. The alkylmethacrylates and alkylacrylates wherein alkyl has from 10 to 20 carbon atoms are more preferred. Dodecyl methacrylate and N-dodecyl methacrylamide are the most preferred where hydrolysis is not a problem.

Suitable water-soluble monomers include those ionizable or hydrolyzable monomers which are sufficiently water-soluble to form at least a 10 weight percent solution when dissolved in water and readily undergo addition polymerization to form polymers which are water-soluble. Exemplary water-soluble monomers include ethylenically unsaturated carboxylic acids such as acrylic acid, methacrylic acid, itaconic acid and fumaric acid; ethylenically unsaturated amides such as acrylamide, methacrylamide and fumaramide and their N-substituted derivatives such as 2-acrylamido-2-methylpropane sulfonic acid (AMPS), N-(dimethylaminomethyl)acrylamide as well as N-(trimethylammoniummethyl)acrylamide chloride and N-(trimethylammoniumpropyl)methacrylamide chloride; and other ethylenically unsaturated quaternary ammonium compounds such as vinylbenzyl trimethyl ammonium chloride; sulfoalkyl esters of unsaturated carboxylic acids such as 2-sulfoethyl methacrylate, aminoalkyl esters of unsaturated carboxylic acids such as 2-aminoethyl methacrylate; vinyl amines such as vinyl pyridine and vinyl morpholine; diallyl amines and diallyl ammonium compounds such as diallyl dimethyl ammonium chloride, vinyl heterocyclic amides such as vinyl pyrrolidone, vinylaryl sulfonates such as vinylbenzyl sulfonate; as well as the salts of the foregoing monomers. Preferable salts unclude the sodium, potassium and ammonium salts of the monomers. Of the foregoing water-soluble monomers, acrylic acid, including salts of acrylic acid such as sodium acrylate or ammonium acrylate, and acrylamide and combinations of these are preferred. Hydrolyzable monomers can also be employed.

The hydrophilic/hydrophobic polymer is preferably an addition copolymer of a water-soluble ethylenically unsaturated monomer and an ethylenically unsaturated monomer having sufficient concentration of hydrophobic groups to enable the resulting polymer to form a gel under conditions of use. Exemplary preferred polymers include copolymers of from about 90 to about 99.995, more preferably from about 98 to about 99.995, most preferably from about 99 to 99.9, mole percent of one or more water-soluble monomers with from about 0.005 to about 10, more preferably from about 0.005 to 2, most preferably from 0.1 to about 1, mole percent of one or more hydrophobic monomers. For these polymers, preferred amounts of hydrophobic monomers can vary with the molecular weight of the polymer.

The crosslinking can be provided by a variety of means. See, for example, U.S. Pat. No. 4,293,609. The amount of crosslinking can vary and can suitably range from about 0 to about 5 weight percent, preferably from about 300 to about 3,000 ppm of crosslinkable monomer, based on all polymerized monomers. Preferably, the crosslinking agent is a polyvinyl monomer. Examples of polyvinyl monomers include divinyl benzene, acryloyl or methacrylyl polyesters of polyhydroxylated compounds, divinyl esters of polycarboxylic acid, diallyl esters of polycarboxylic acids, diallyl dimethyl ammonium chloride, triallyl terephthalate, methylene bisacrylamide, diallyl maleate, diallyl fumarate, hexamethylene bis maleimide, triallyl phosphate, trivinyl trimellitate, divinyl adipate, glyceryl trimethacrylate, diallyl succinate, divinyl ether, the divinyl ethers of ethylene glycol or diethylene glycol diacrylate, polyethylene glycol diacrylates or methacrylates, 1,6-hexanediol diacrylate, pentaerythritol triacrylate or tetracrylate, neopentyl glycol diacrylate, cyclopentadiene diacrylate, the butylene glycol diacrylates or dimethyacrylates, trimethylolpropane di- or tri-acrylates, and the like.

The polymers of this invention can be prepared using aqueous solution techniques, inverse bead suspension techniques, spray bead polymerization techniques using UV catalysis, or other such techniques. Preferred methods of preparation include those aqueous solution techniques.

The aforementioned hydrophilic/hydrophobic polymers containing hydrophobic moieties are advantageously prepared by copolymerizing the water-soluble monomers with hydrophobic monomers in an aqueous medium containing an ionic surfactant or emulsifier that solubilizes the hydrophobic monomer in the aqueous medium. By solubilizing the hydrophobic monomer in the aqueous medium, it is meant the combination of aqueous medium, hydrophobic monomer and emulsifier gives the visual appearance of a clear or translucent solution. That is, a micelle forming amount of a surfactant is employed. This copolymerization is preferably accomplished in an aqueous medium containing a polymerization initiator capable of generating free-radicals. Optionally, a chain transfer agent may be included in the polymerization reaction mixture.

The solubilizing surfactant or emulsifier is required in most instances to suitably solubilize the hydrophobic monomer and to subsequently obtain a hydrophilic/hydrophobic polymer having a desirable concentration of hydrophobic moieties in the polymer. It is believed that the hydrophobic monomer is solubilized in the micelles formed by the emulsifier. Thus, the emulsifier is generally employed in an amount which is above the critical micelle concentration (CMC) of the emulsifier or emulsifier mixture, but less than that which reduces the concentration of hydrophobic monomer in the resultant hydrophilic/hydrophobic polymer to a point that the polymer will not form a gel under the conditions which the product is used. The amount of emulsifier used will also be such that there is believed to be at least one hydrophobic monomer molecule per micelle of the emulsifier. An upper limit to the amount of hydrophobic monomer which is employed is based on that level which can be solubilized by the surfactant, i.e., an amount of hydrophobic monomer below which the reaction mixture becomes cloudy. For example, when sodium dodecyl sulfate (NaDS) is employed as an emulsifier for dodecyl methacrylate (DMA), the molar ratio of DMA to NaDS is at least 1:50 up to about 1:2, preferably from 1:5 to 1:25, most preferably about 1:10 to about 1:15. By knowing the CMC, the hydrophilic-lipophilic balances (HLB) and aggregation number of molecules in the micelle molecular weight of an emulsifier and the hydrophobicity of the hydrophobic monomer, suitable molar ratios and appropriate emulsifier concentrations can be determined for any given hydrophobio monomer and emulsifier to provide similar suitable concentrations of hydrophobic moieties in the hydrophilic/hydrophobic polymer.

Suitable emulsifiers include anionic agents such as alkali metal salts of alkyl sulfates and alkyl and aryl sulfonates, e.g., dodecyl alkyl sulfosuccinates and sodium dodecylbenzene sulfonate; fatty acid soaps, e.g., sodium oleate, sodium stearate and potassium oleate; alkali metal salts of sulfonated fatty alcohols, e.g., sodium dodecyl sulfate; sulfates of ethoxylated alcohols; alkyl phosphate esters, e.g., dodecyl hydrogen phosphate; fluoro emulsifiers, e.g., perfluoroalkyl sulfates; and the like. Also included are cationic emulsifiers such as alkylamine hydrochlorides, e.g., dodecylamine hydrochloride and tridecylamine hydrochloride; quaternary alkyl or aryl ammonium halides such as dodecyl trimethyl ammonium chloride; ethoxylated fatty amines and other emulsifiers as described in *McCutcheon's Detergents and Emulsifiers*, North American Edition, 1980 Annual. In general, when the hydrophilic/hydrophobic polymer is anionic or nonionic, an anionic emulsifier such as an alkali metal alkyl sulfate is preferably employed as the emulsifier. When the hydrophilic/hydrophobic polymer is cationic, a cationic emulsifier such as dodecylamine hydrochloride is preferably employed. When the hydrophilic/hydrophobic polymer is nonionic, anionic or cationic, a nonionic emulsifier such as nonylphenoxy polyethylene glycol having 10 ethyleneoxy units per molecule or other water-dispersible nonionic surfactants as defined herein can be employed subject to the condition that an ionic surfactant be employed.

Exemplary suitable polymerization initiators include the azo catalysts such as azobisisobutyronitrile, 2,2¹-azobis(2,4-dimethylpentanenitrile) and dimethyl azoisobutyrate; organic peroxygen compounds such as benzoyl peroxide, t-butyl peroxide, diisopropyl benzene hydroperoxide and t-butyl hydroperoxide; and inorganic persulfates such as potassium persulfate, ammonium persulfate and sodium persulfate. Of these initiators, the oil-soluble types such as the organic peroxides and azo compounds are preferred. It is desirable to employ from about 0.01 to about 0.1 weight percent of initiator based on the monomers.

In an optional embodiment, a nonionic surfactant is added to the polymerization recipe as another component in addition to the ionic surfactant, i.e., emulsifier. Alternatively, it is suitable to add the nonionic surfactant to the hydrophilic/hydrophobic polymer subsequent to polymerization. Exemplary nonionic surfactants include the reaction products of ethylene oxide or mixtures of ethylene oxide and higher alkylene oxide with active hydrogen compounds such as phenols, alcohols, carboxylic acids and amines, e.g., alkylphenoxyethyleneoxy ethanols. More preferred nonionic surfactants are the alkyl polyethyleneoxy compounds represented by the formula:

$$RO(EO)_n-H$$

wherein R is $C_8-C_{18}$ alkyl, EO is ethyleneoxy and n is a number from 1 to 10. Other suitable nonionic surfactants are described in McCutcheon's, supra. Of the foregoing surfactants, the ethoxylated alkyl phenol and ethoxylated fatty alcohols are more preferred.

Suitable anionic substituted polyethyleneoxy compounds useful herein are represented by the formula:

$$RO(EO)_n-X$$

wherein R and n are as defined hereinbefore, EO is ethyleneoxy and X is $SO_3H$ or $CH_2CO_2H$ or $PO_3H$; salts of long chain carboxylates such as potassium oleate, sodium laurate, potassium stearate, potassium caprolate, sodium palmatate and the like; alkali metal alkylbenzene sulfonates such as sodium nonylbenzene sulfonate and potassium dodecylbenzene sulfonate; alkali metal alkyl sulfates such as sodium dodecyl sulfate and alkali metal dialkyl sulfosuccinates such as sodium dihexyl sulfosuccinate and sodium dioctyl sulfosuccinate; salts of resin acids such as abietic acid and dihydroabietic acid.

The hydrophilic/hydrophobic polymers when made using unneutralized acidic monomers are conveniently neutralized using organic or inorganic bases, by mixing the polymer with the base. Bases such as ammonia, ammonium hydroxide, alkali metal hydroxides, alkali metal bicarbonates, carbonates, alkali metal salts of basic phosphates, silicates, organic amines such as alkyl amines, alkanol amines, and other similar bases can be used. It is also understood that the polymer can be neutralized after recovering the polymer, if so required. The degree of neutralization in the polymers can vary from about 0 to about 100 percent, preferably from about 50 to about 80 percent.

The hydrophilic/hydrophobic polymers are readily recovered from the aqueous medium when such is desired by removal of water under vacuum or by azeotropic distillation or by drum drying. The polymer can be ground to the desired size (e.g., such as a powder, prior to use).

It is also understood that hydrophilic/hydrophobic polymers of monomers such as acrylamide or methylacrylate, acrylic acid and hydrophobic monomer can be prepared by copolymerizing all three of these monomers or by copolymerizing acrylamide or methylacrylate with the hydrophobic monomer and subsequently hydrolyzing a portion of the copolymerized hydrolyzable monomer such as acrylamide or methylacrylate by contacting the copolymer with a base such as sodium hydroxide and/or sodium carbonate.

The inorganic colloidal support is preferably a water-insoluble material which has a particle size small enough that the particles disperse in an aqueous solution to yield transparent or translucent fluids. Typical colloidal particles which are useful as colloidal supports are inorganic materials having a particle diameter from about 50 Å to about 200 Å, preferably from about 80 Å to about 100 Å. Clusters of particles are not generally larger than 1,000 Å in diameter. Colloidal support can be any substantial water-insoluble inorganic materials.

Suitable materials include colloidal or fumed silica, alumina, titania, and the like, as well as colloidal oxide sols such as those containing zinc, zirconium, nickel, iron, cobalt, and the like.

The polymer can be blended with the colloidal support using a variety of techniques. For example, the support and polymer can be dry blended. Most preferably, the support is dispersed in an aqueous liquid and contacted with the polymer, which is either in gel state or dry state. The support and polymer mixture can be dried, if desired. It is also possible to polymerize the monomers in the presence of a dispersed colloidal support.

The amount of colloidal support which is employed can vary. Suitable amounts of colloidal support range from 0 to about 80, preferably from about 0.2 to about 50, weight percent based on the weight of polymer and support. Such compositions can exhibit increased gel strengths over those compositions not containing the colloidal support.

The compositions of this invention can be further, though optionally, blended with a desired inorganic filler which can be non-colloidal in nature. Although the materials can be physically blended using a wide variety of means, dry blending is preferred. That is, essentially dry polymer is physically mixed with the desired filler which is essentially dry inorganic powder. Thorough mixing insures good gel strength of the composition. Generally the order of addition of components is not particularly critical. More preferably, the filler is added to the components present in the polymerization recipe before total polymerization has occurred.

By the term "filler" is meant a very finely divided water insoluble or sparingly water-soluble grouping or aggregate of solid particles, usually smaller than 1,000 $\mu$m but which is not generally colloidal in nature. Inorganic powders especially preferred herein include alumina trihydrate and a wide variety of clays. Specific examples include sodium bentonite (montmorillonite clay), kaolinite and attapulgite. Other inorganic powders include, for example, white carbon, synthetic silicate white carbon, basic magnesium carbonate, ultrafine magnesium silicate, light or heavy calcium carbonate, soft or hard clays, talc, vermiculite, pearlite, barium sulfate, mica, and the like.

The amount of polymer and optional colloidal support employed in blends with filler can preferably range from about 20 to about 100, most preferably from about 40 to about 75, especially preferably from about 60 to about 70, weight percent of polymer and colloidal support based on the total weight of the polymer, colloidal support and filler. Conversely, the amount of filler useful herein preferably ranges from about 0 to about 80, most preferably from about 25 to about 60, especially preferably from about 30 to about 40, weight percent of said filler based on the total weight of the polymer, colloidal support and filler.

Such blended compositions (i.e., containing polymer, optional colloidal support and filler) can exhibit further increased gel strengths over those compositions containing a polymer and not containing the inorganic filler. The high gel strengths of such compositions allow for products exhibiting good utilization of water absorbent capacity as well as good integrity. In this regard, the compositions of this invention are easy to handle and can be employed in a wider variety of applications than have those previously employed water absorbent materials.

The compositions of this invention can be incorporated into film laminates and other such materials as are described, for example, in U.S. Pat. Nos. 4,117,184; 4,176,677; 4,293,609 and 4,424,247, which are incorporated herein by reference. For example, polymer compositions can be incorporated in wicking substrates and treated as described in U.S. Pat. No. 4,293,609. Such materials exhibit high water absorbent capabilities. The compositions of this invention and the laminates prepared therefrom can be incorporated into absorbent devices. The compositions can be used in those applications which have employed hydrophilic polymers as highly absorbent materials. The compositions can be employed in conjunction with water-absorbent polymeric materials known in the art, as for example, polymeric blends.

The compositions of this invention can be shaped and formed for use in a wide variety of applications. For example, the compositions can be formed into sheets, filaments, coatings or molded articles. The compositions can be foamed, extruded into articles or extruded into a pellet form. The compositions of this invention can be incorporated into a wide variety of product forms.

Use of the increased gel strength composition of the present invention include applications such as shut-off filters for fuels such as gasoline, oil, hydraulic fluids, and the like. Other applications include the incorporation of such compositions, as is necessary, in disposable diapers, tampons, and other personal hygiene products and applications.

The following examples are presented to further illustrate but not limit the scope of this invention. All parts and percentages are given based on weight, unless otherwise noted.

EXAMPLE 1

A clear mixture of 1.05 grams (g) lauryl methacrylate in 12.5 g of a 30 percent solution of sodium lauryl sulfate is charged to a one-half liter jacketed reactor equipped with a stirrer, nitrogen sparge tube, gas outlet and thermometer. To the reactor is charged 270 g deionized water, 36 g acrylic acid, and 0.024 g of active 2,2$^1$-azobis(2,4-dimethylpentanenitrile) dissolved in 1 g polyethylene glycol of secondary alcohol surfactant. The reaction mixture is sparged with nitrogen. The reactor jacket is brought to 60° C. and this temperature is maintained for 4 hours. The resulting gel is neutralized using 22.8 g of a 28.4 percent active aqueous ammonia solution. The neutralized gel is dried on a steam heated rotating drum apparatus. The resulting flake material is ground in a Waring Blendor and screened such that particles having a size of less than 20 mesh are obtained.

The free swell capacity of the polymer (i.e., the grams of fluid absorbed per gram of polymer) is determined by dispersing 0.5 g of polymer in 150 g of a 1 percent aqueous sodium chloride solution, waiting 20 minutes, removing nonabsorbed water by pouring the mixture into a funnel lined with a 150 micron nylon screen, allowing free water to drain for 20 minutes, and weighing the drained (i.e., nonabsorbed) water. After drainage the gel is tough and firm indicating good gel strength. The free swell capacity of the product is 54.

EXAMPLE 2

A mixture of 1.05 g lauryl methacrylate in 6.25 g of a 60 percent solution of sodium dodecyl benzene sulfonate is charged into a reactor, as described in Example 1. To the reactor is charged 306 g deionized water, 36 g acrylic acid and 0.048 g of active catalyst dissolved in 1 g surfactant, as described in Example 1. The mixture is subjected to polymerization conditions and isolated, as in Example 1. The free swell capacity of the product is 97, as determined as described in Example 1.

EXAMPLE 3

A mixture of 0.75 g stearylmethacrylate in 6 g of a 30 percent solution of sodium lauryl sulfate is charged into a reactor, as described in Example 1. To the reactor is charged 315 g deionized water, 36 g acrylic acid and 0.024 g of active catalyst dissolved in 1 g surfactant, as described in Example 1. The mixture is subjected to polymerization conditions and isolated, as in Example 1. The free swell capacity of the product is 91, as determined as described in Example 1.

EXAMPLE 4

A mixture of 0.63 g laurylmethacrylate in 6.25 g of a 30 percent solution of sodium lauryl sulfate is charged into a reactor, as described in Example 1. To the reactor is charged 275 g deionized water, 36 g acrylic acid and 0.038 g of active catalyst dissolved in 1 g surfactant, as described in Example 1. To the mixture is added 15.4 g of alumina trihydrate. The mixture is subjected to polymerization conditions and isolated, as in Example 1. The free swell capacity of the product is 70, as determined as described in Example 1.

EXAMPLE 5

Into a citrate bottle is charged 99 parts acrylic acid as about a 40 percent aqueous solution. The citrate bottle contains 10 parts sodium lauryl sulfate, 9.6 parts based on monomer of a nonionic surfactant represented as $C_{12}H_{25}(EO)_5$—H, 6.4 parts based on monomer of a nonionic surfactant represented as $C_{12}H_{25}(EO)_{10}$—H, and 1 mole percent lauryl methacrylate. The solution is stirred and 500 parts methylene bisacrylamide based on monomer is added as an aqueous solution having a concentration of 1.25 percent in water. To this mixture is added 1,000 ppm based on monomer of an azobisisobutyronitrile catalyst as a 1.25 percent solution in t-butyl alcohol. Distilled water is added to bring the monomer concentration of the mixture to 10 percent. The bottle is purged with nitrogen and the bottle is capped. The contents are subjected to polymerization conditions at 60° C. for 18 hours. The product is a thick gel which is drum dried and ground to 20 mesh particle size. The product is designated as Sample A. Gel capacity of this product is determined to be 70 g of absorbed 1 percent aqueous sodium chloride solution per gram of product. Gel capacity is determined by contacting about 0.2 g of product with about 25 g of said solution for about 20 minutes. The mixture is drained on a 20 mesh screen and weighed.

Gel strength of this wet gel is determined to be 1.1 pounds per square inch. Gel strength is determined by placing weight on a piston placed over the gel until gel begins to extrude through the 20-mesh screen that the gel rests on.

For comparison purposes, an acrylic acid polymer crosslinked with 500 ppm methylene bisacrylamide yields a slimy product upon contact with the sodium chloride solution, and exhibits a gel strength of less than 0.4 pounds per square inch.

EXAMPLE 6

A produot is prepared and evaluated as described in Example 5, except that the recipe includes 1,000 ppm methylenebisacrylamide rather than 500 ppm. The product is designated Sample B. The gel capacity of the product is 45 g of percent of absorbed sodium chloride solution per gram of product. The gel strength of the product is 1.1 pounds per square inch, determined as described in Example 5.

For comparison purposes, an acrylic acid polymer crosslinked with 1,000 ppm methylene bisacrylamide yields a slimy product upon contact with the 1 percent sodium chloride solution, and exhibits a gel strength of less than 0.4 pounds per square inch.

EXAMPLE 7

To each of 0.2 g of product samples in Examples 5 and 6 are added 2.5 g of a 2 percent dispersion of colloidal silica in a 1 percent aqueous sodium chloride solution. The product and dispersion are mixed, and to the mixture is added a few drops of ammonium hydroxide solution. Gel capacity of the sample is determined as described in Example 5, and is determined to be 75 g of 1 percent aqueous sodium chloride solution per gram of polymer for Sample A. The gel strength of Sample A which is mixed with the colloidal silica is 2.75 pounds per square inch. Gel capacity is determined to be 80 g of 1 percent aqueous sodium chloride solution per gram of polymer for Sample B which is treated with the colloidal silica. The gel strength of Sample B which is similarly mixed with the colloidal silica is 3.75 pounds per square inch.

What is claimed is:

1. A composition capable of absorbing an aqueous liquid which composition comprises a functionally effective amount of a swellable addition polymer comprising, in polymerized form, (a) a major portion of at least one water-soluble monomer, (b) a minor portion of at least one water-insoluble monomer having a pendant hydrophobic moiety, and optionally, (c) a minor portion of a crosslinking moiety in an amount sufficient to provide gel strength to the polymer; which polymer is polymerized in the presence of at least a micelle forming amount of a surfactant composition containing at least one ionic surfactant; and which polymer is capable of undergoing hydrophobic association through hydrophobic groups of said polymer such that said polymer is swellable but not readily soluble in the presence of an aqueous liquid when said polymer is in intimate contact with an amount of surfactant, if any, which is less than that amount of surfactant which will solubilize said polymer in said aqueous liquid.

2. A composition of claim 1 wherein said polymer comprises, in polymerized form, from about 90 to about 99.995 mole percent of at least one water-soluble monomer, and from about 0.005 to about 10 mole percent of at least one monomer having a pendent hydrophobic moiety.

3. A composition of claim 1 wherein said polymer comprises, in polymerized form, from about 98 to about 99.995 mole percent of at least one water-soluble monomer, and from about 0.005 to about 2 mole percent of at least one monomer having a pendent hydrophobic moiety.

4. A composition of claim 1 wherein said monomer having a pendant hydrophobic moiety is derived from the reaction of alkanols having from 4 to about 20 carbon atoms with an ethylenically unsaturated carboxylic acid.

5. A composition of claim 1 wherein said monomer having a pendant hydrophobic moiety is an alkylacrylate or alkylmethacrylate wherein alkyl has about 4 to about 20 carbon atoms.

6. A composition of claim 1 wherein said water-soluble monomer is ionic in character.

7. A composition of claim 1 wherein said water-soluble monomer is anionic in character.

8. A composition of claim 7 wherein the ionic surfactant is an anionic surfactant.

9. A composition of claim 1 wherein said polymer comprises, in polymerized form, from about 90 to about 99.995 mole percent of at least one water-soluble monomer, from about 0.005 to about 10 mole percent of at least one monomer having a pendant hydrophobic moiety, and from about 0 to about 50,000 ppm of crosslinkable monomer.

10. A composition of claim 9 wherein said crosslinkable monomer is a polyvinyl monomer.

11. A composition of claim 1 wherein said polymer comprises, in polymerized form, from about 90 to about 99.995 mole percent of at least one water-soluble monomer, from about 0.005 to about 10 mole percent of at least one monomer having a pendant hydrophobic moiety, and from about 300 to about 3,000 ppm of crosslinkable monomer.

12. A composition capable of absorbing an aqueous liquid which composition comprises a polymer of claim 1 and a functionally effective amount of an inorganic colloidal support.

13. A composition of claim 12 comprising from about 20 to about 100 weight percent polymer and from about 0 to about 80 weight percent colloidal support, based on the weight of the polymer and colloidal support.

14. A composition of claim 12 comprising from about 50 to about 90 weight percent polymer and from about 10 to about 50 weight percent colloidal support, based on the weight of the polymer and colloidal support.

15. A laminated article capable of absorbing aqueous fluids comprising the composition of claim 1.

16. A laminated article capable of absorbing aqueous fluids comprising the composition of claim 12.

17. A composition of claim 12 wherein said colloidal support comprises particles having a diameter from about 50 Å to about 200 Å.

18. An absorbent device comprising the composition of claim 1.

19. An absorbent device comprising the composition of claim 12.

20. An absorbent device comprising the composition of claim 15.

21. An absorbent device comprising the composition of claim 16.

22. A process for absorbing aqueous fluids by contacting said fluids with the composition of claim 1.

23. A process for absorbing aqueous fluids by contacting said fluids with the composition of claim 12.

24. A composition of claim 7 wherein said monomer is the neutralized form of acrylic acid or methacrylic acid.

25. A composition of claim 1 wherein said minor amount of said monomer having a pendant hydrophobic moiety in an amount which can be solubilized by said micelle forming amount of surfactant composition containing at least one ionic moiety.

26. A composition of claim 1 wherein said crosslinking moiety is a polyvinyl monomer.

27. A process for providing a swellable addition polymer for use in a composition capable of absorbing an aqueous liquid, said process comprising providing (1) (a) a major portion of at least one water-soluble monomer, (b) a minor portion of at least one water-soluble monomer having a pendant hydrophobic moiety, and optionally, (c) a minor portion of a crosslinking moiety, and (2) polymerizing said monomers in an aqueous medium in the presence of at least a micelle forming amount of a surfactant composition containing at least one ionic surfactant such that the resulting polymer is capable of undergoing hydrophobic association through hydrophobic groups of said polymer, and wherein said polymer is swellable but not readily soluble in the presence of an aqueous liquid when said polymer is in intimate contact with an amount of surfactant, if any, which is less than that amount of surfactant which will solubilize said polymer in said aqueous liquid.

* * * * *

UNITED STATES PATENT AND TRADEMARK OFFICE
CERTIFICATE OF CORRECTION

PATENT NO. : 4,535,098

DATED : August 13, 1985

INVENTOR(S) : Syamalarao Evani et al.

It is certified that error appears in the above-identified patent and that said Letters Patent is hereby corrected as shown below:

Col. 12, Claim 27, line 30, "water-soluble" should read --water-insoluble--.

Signed and Sealed this

Seventh Day of October, 1986

[SEAL]

Attest:

DONALD J. QUIGG

Attesting Officer

Commissioner of Patents and Trademarks